(12) United States Patent
McNamara et al.

(10) Patent No.: US 7,053,121 B2
(45) Date of Patent: May 30, 2006

(54) COMPOSITIONS AND METHODS FOR REGULATING CIRCADIAN RHYTHMS

(75) Inventors: Peter J. McNamara, San Diego, CA (US); Garret A. FitzGerald, Wayne, PA (US); Deba Chakravarti, Swarthmore, PA (US); Amita Sehgal, Haverford, PA (US)

(73) Assignee: Trustees of the University of Pennsylvania, Philadelphia, PA (US)

( * ) Notice: Subject to any disclaimer, the term of this patent is extended or adjusted under 35 U.S.C. 154(b) by 429 days.

(21) Appl. No.: 10/102,430

(22) Filed: Mar. 19, 2002

(65) Prior Publication Data

US 2002/0151590 A1    Oct. 17, 2002

Related U.S. Application Data

(60) Provisional application No. 60/277,328, filed on Mar. 19, 2001.

(51) Int. Cl.
*A61K 3/127* (2006.01)
*A61K 31/00* (2006.01)
*A61K 31/20* (2006.01)
*A61K 31/07* (2006.01)

(52) U.S. Cl. .................. 514/559; 514/1; 514/725; 424/450

(58) Field of Classification Search ........... 424/450; 514/725, 559, 1
See application file for complete search history.

(56) References Cited

U.S. PATENT DOCUMENTS 5,811,119 A * 9/1998 Mehta et al. ............... 424/450
6,468,756 B1 * 10/2002 Bonini et al. ............... 435/7.1

OTHER PUBLICATIONS

McNamara P et al. Regulation of CLOCK and MOP4 by nuclear hormone receptors in the vasculature: a humoral mechanism to reset a peripheral clock. Cell. Jun. 29, 2001;105(7):877-89.*

Stroup D et al. Orphan receptors chicken ovalbumin upstream promoter transcription factor II (COUP-TFII) and retinolid X receptor (RXR) activate and bind the rat cholesterol 7alpha-hydroxylase gene (CYP7A). J Biol Chem. Apr. 11, 1997;272(15):.*

Becker-Andre M et al. Pineal gland hormone melatonin binds and activates an orphan of the nuclear receptor superfamily. J Biol Chem. Nov. 18, 1994;269(46):28531-4.*

André et al., "Disruption of retinoid-related orphan receptor β changes circadian behavior, causes retinal degeneration and leads to vacillans phenotype in mice", The EMBO Journal 1998 17(14) :3867-3877.

Flower D.R., "The lipocalin protein family:structure and function", Biochem. J. 1996 318:1-14.

Fu et al., "Regulation of the expression of serotonin N-acetyltransferase gene in Japanese quail (*Coturnix japonica*) :II. Effect of vitamin A deficiency", J. Pineal Res. 1999 27:34-41.

Gu et al., "The PAS Superfamily:Sensors of Environmental and Developmental Signals", Annu. Rev. Pharmacol. Toxicol. 2000 40:519-561.

Liu et al., "Cellular Construction of a Circadian Clock: Period Determination of the Suprachiasmatic Nuclei", Cell 1997 91:855-860.

Rajendran et al., "Zebrafish Interphotoreceptor Retinoid-Binding Protein:Differential Circadian Expression Among Cone Subtypes", The Journal of Experimental Biology 1996 199:2775-2787.

Sarov-Blat et al., The Drosophila takeout Gene Is a Novel Molecular Link between Circadian Rhythms and Feeding Behavior, Cell 2000 101:647-656.

Soprano et al., "Plasma Retinol-Binding Protein", RETINOIDS:Biology, Chemistry and Medicine 2nd Edition 1994.

Welsh et al., "Individual Neurons Dissociated from Rat Suprachiasmatic Nucleus Express Independently Phased Circadian Firing Rhythms", Neuron 1995 14:697-706.

* cited by examiner

*Primary Examiner*—Joseph Murphy
(74) *Attorney, Agent, or Firm*—Licata & Tyrrell P.C.

(57) ABSTRACT

The present invention provides methods of effecting a change in the core circadian clock by modulating retinoid nuclear receptors.

6 Claims, 5 Drawing Sheets

COMPOSITIONS AND METHODS FOR REGULATING CIRCADIAN RHYTHMS

INTRODUCTION

This application claims the benefit of priority of U.S. provisional application Ser. No. 60/277,328, filed on Mar. 19, 2001, which is incorporated herein in its entirety.

This invention was made in the course of research sponsored by the National Institutes of Health (NIH Grant No. 5-P50-HL-16-54500-06). The U.S. government may have certain rights to this invention.

BACKGROUND OF THE INVENTION

The internal circadian clock is a molecular time-keeping mechanism that generates a biological rhythm, regulating diverse physiological processes such as blood pressure, sleep-wake cycles and body temperature in mammals (Dunlap (1999) Cell 96:271–290; Cermakian, et al. (2000) Nature Reviews Molecular Cell Biology 1:59–67; King, et al. (2000) Annu. Rev. Neurosci. 23:713–742). Circadian clocks have been conserved throughout evolution and are present in almost all living organisms. The master pacemaker resides in the suprachiasmatic nucleus (SCN) in mammals (Reppert, et al. (1997) Cell 89:487–490). The SCN consists of multiple, single-cell circadian oscillators, which operate in a cell autonomous fashion. They are synchronized to fire rhythmically, generating a coordinated, circadian, rhythmic output in intact animals (Welsh, et al. (1995) Neuron 14:697–706; Liu, et al. (1997) Cell 91:855–860). Dawn and dusk coordinate or entrain the circadian clock through neural pathways connecting the retina to the SCN, so that the master clock and its output rhythms do not drift from a 24 hour cycle, but remain aligned with the solar day. Transient disruption of circadian timing following transmeridian flights leads to jet lag, and chronic alterations of the central clock mechanism of shift workers, which is approximately 25% of the working population, may contribute to poor health and sleep disorders. Moreover, specific rhythm defects may be involved in neuropsychiatric illnesses. Therefore, the need exists to develop mechanisms of regulating the circadian rhythm in humans.

Interacting positive and negative transcriptional-translational feedback loops drive circadian oscillations in both *Drosophila* and mammals. The best-characterized feedback loop in mice, involves the regulation of three Period genes (mPER1–3) and two Cryptochrome genes (mCRY1 and mCRY2)(Todo, et al. (1996) Science 272:109–112; Shearman, et al. (1997) Neuron 19:1261–1269; Sun, et al. (1997) Cell 90:1003–1011; Tei, et al. (1997) Nature 389:512–516; van der Horst, et al. (1999) Nature 398:627–630). The positive limb of this feedback loop requires the function of two basic helix-loop-helix-PAS (bHLH-PAS) proteins, CLOCK and BMAL1 (also known as MOP3) (King, et al. (1997) Cell 89:641–653; Gekakis, et al. (1998) Science 280:1564–1569; Hogenesch, et al. (1998) Proc. Natl. Acad. Sci. USA 95:5474–5479). It is believed that transcription of mPer and mCry is driven by accumulating CLOCK:BMAL heterodimers, which, in turn bind to consensus E-box elements (CACGTG) in their promoter regions (Darlington, et al. (1998) Science 280:1599–1603; Jin, et al. (1999) Cell 96:57–68). Heteromultimeric complexes formed from the products of the mPER and mCRY genes enter the nucleus, where the mCRY proteins shut off CLOCK:BMAL1-mediated transcription. At the same time, mPER2 increases levels of Bmal1 RNA through an as yet uncharacterized mechanism. This leads ultimately to renewal of BMAL1 levels, which increase CLOCK:BMAL1 heterodimers to drive mPer/mCRY transcription and restart the cycle (Kume, et al. (1999) Cell 98:193–205; Shearman, et al. (2000) Science 288:1013–1019). MOP4 (also termed NPAS2) is another member of the bHLH-PAS family of transcription factors and shares high homology at the amino acid level with CLOCK (Hogenesch, et al. (1997) J. Biol. Chem. 272: 8581–8593; Zhou, et al. (1997) Proc. Natl. Acad. Sci. USA 94:713–718). In cultured cells, MOP4, like CLOCK, also functions optimally as a heterodimeric partner to BMAL1. The MOP4:BMAL1 heterodimer recognizes the same consensus E-box element as CLOCK:BMAL1 (Hogenesch, et al. (1998) Proc. Natl. Acad. Sci. USA 95:5474–5479), and CRY1 and CRY2 can inhibit MOP4:BMAL1-dependent E-box activation of genes such as Per1 and vasopressin (Kume, et al. (1999) Cell 98:193–205). However, the low level of MOP4 expression (Hogenesch, et al. (1998) Proc. Natl. Acad. Sci. USA 95:5474–5479) and the absence of mRNA cycling in the SCN (Shearman, et al. (1999) Neuroscience 89:387–397) has put into question its involvement in the core circadian feedback loop. Initially, it was believed that clock proteins were present only in specialized pacemaker neurons, such as those within the SCN. Recently, however, molecular clocks similar to those operating in SCN neurons have been uncovered in peripheral tissues (Zylka, et al. (1998) Neuron 20:1103–1110) and even in immortalized rat-1 fibroblast cell-lines (Balsalobre, et al. (1998) Cell 93:929–937). In peripheral tissues, such as the liver, kidney, and heart, circadian rhythms in RNA abundance are apparent for each of the mPER genes, although the phase of oscillation is delayed 3–9 hours relative to the oscillation in the SCN (Zylka, et al. (1998) Neuron 20:1103–1110). Clock gene oscillations are lost in SCN-lesioned animals (Sakamoto, et al. (1998) J. Biol. Chem. 273:27039–27042). Furthermore, gene oscillations dampen more rapidly in cultures of peripheral tissues than SCN cells in vitro, where they are sustained for weeks (Yamazaki, et al. (2000) Science 288: 682–685). This suggests that the peripheral oscillations may be driven or synchronized by the SCN. It has been suggested that the SCN clock may synchronize peripheral clocks via both neural and hormonal signals (Ikonomov, et al. (1998) Prog. Neurobiol. 54:87–97; Ishida, et al. (1999) Proc. Natl. Acad. Sci. USA 96:8819–8820; Akashi, et al. (2000) Genes Dev. 14:645–649). Examples of stimuli that phase-shift central circadian oscillators include vasoactive intestinal peptide (Watanabe, et al. (2000) Brain Res. 877:361–366), delta opioid agonists (Byku, et al. (2000) Brain Res. 873: 189–196), neuropeptide Y (Yannielli, et al. (2000) Neuroreport 11:1587–1591), and GABA (Liu, et al. (2000) Neuron 25:123–128). Steroid hormones and catecholamines are attractive candidate regulators of peripheral clocks and examples of hormonal phase-shifting of circadian genes in peripheral organs have begun to emerge (Balsalobre, et al. (2000) Science 289:2344–2347). Circulating concentrations of both steroids and catecholamines undergo circadian variability (Tronche, et al. (1998) Curr. Opin. Genet. Dev. 8:532–538; Czeisler, et al. (1999) Recent Prog. Horm. Res. 54:97–130; McCarty, et al. (1981) Physiol. Behav. 26:27–31; Muller (1999) Am. J. Hypertens. 12:35S-42S). While catecholamines can regulate gene expression via signaling cascades downstream of membrane receptors (Weiner and Molinoff (1995) Catecholamines. In: Basic Neurochemistry: Molecular Cellular and Medical Aspects, G. J. Siegel, ed. (New York, N.Y.; Raven press), pp. 276–312), steroid hormones function by activating nuclear hormone receptors (Perlmann, et al. (1997) Cell 90:391–397) which function as ligand-dependent transcription factors (Lin, et al. (1998) Cold Spring Harb. Symp. Quant. Biol. 63:577–585).

Though there is no molecular data, several lines of evidence suggest that a vascular clock exists. For example, blood pressure undergoes a marked circadian variability (Millar-Craig, et al. (1978) *Lancet* 1:795–797; Panza, et al. (1991) *N. Engl. J. Med.* 325:986–990), which is increased in patients with hypertension (Lemmer (1999) *Acta Physiol. Pharmacol. Bulg.* 24:71–80) and coincides with a temporal variability in the incidence of acute vascular events, such as myocardial infarction, sudden cardiac death and stroke (Marshall (1977) *Stroke* 8:230–231; Tsementzis, et al. (1985) *Neurosurgery* 17:901–904; Ridker, et al. (1990) *Circulation* 82:897–902). Evidence also suggests that endothelial function has a circadian variation with attenuated activity in the morning (Elherik, et al. (2000) *Circulation* 102(18):902 Suppl. S). Furthermore, previous studies have shown a circadian variability in the local pressor response to infused catecholamines in humans (Hossmann, et al. (1980) *Cardiovasc. Res.* 14:125–129).

Previous observations have hinted at a circadian role for retinoid nuclear receptors and vitamin A. For example, targeted gene disruption of the retinoid-related orphan receptor, RORβ, extends the period length of the free-running activity rhythm in mice and mildly affects circadian rhythmicity (Andre, et al. (1998) *EMBO J.* 17:3867–3877). Similarly, vitamin A deficiency reduces both the expression of AA-NAT mRNA and melatonin content in the pineal gland (Fu, et al. (1999) *J. Pineal. Res* 27:34–41). The majority of retinol circulates bound to a 21 kDa retinol-binding protein (RBP) (Soprano, et al. (1994) In: The Retinoids, Biology, Chemistry, and Medicine, M. B. Sporn, A. B. Roberts and D. S. Goodman, eds. (New York, N.Y.: Raven Press), pp 257–282), which reportedly undergoes diurnal variation in humans (Hongo, et al. (1993) *J. Nutr. Sci. Vitaminol.* (Tokyo) 39:33–46). Plasma retinol is internalized by cells from RBP through a process involving the action of a number of cellular retinol binding proteins (CRBPs) including the interphotoreceptor retinol binding protein (IRBP), which has been shown to under circadian variation in zebrafish (Rajendran, et al (1996) *J. Exp. Biol* 199:2775–2787). Interestingly, RBP is a member of the lipcalin protein family, as is prostaglandlin $D_2$ synthase (PGDS) (Flower (1996) *Biochem. J.* 318:1–14). Circadian rhythmicity in PGDS expression and consequent biosynthesis of PGD2 is thought to be relevant to regulation of the sleep-wake cycle (Pinzar, et al. (2000) *Proc. Natl. Acad. Sci. USA* 97:4903–4907). In addition, lipocalin protein family resembles the Drosophila takeout (TO) gene superfamily, at least one member of which is controlled by the clock and affects feeding behaviour (Sarov-Blat, et al. (2000) *Cell* 101:647–656); So, et al. (2000) *Mol. Cell Biol.* 20:6935–6944). Some of these observations indicate a role for retinoids, not only in peripheral circadian physiology, but also in functions that may be directly controlled by the brain, however, a molecular mechanism for retinoid action is not known.

Methods of modulating or screening for compounds that modulate the circadian rhythm have focused on CLOCK (U.S. Pat. No. 6,057,125 to Takahaski, et al.), the CLOCK: BMAL1 interaction (PCT Publication WO 99/57137), CRY and PER2 proteins (PCT Publication WO 01/07654), human and mouse PER2 proteins (PCT Publication WO 99/14324), and MOP4 (PCT Publication WO 99/28464). Similarly, modulation of neuropeptide Y Y5 receptor ligand (PCT publication WO 99/05911) and neurokinin-1 receptor antagonist (U.S. Pat. No. 6,274,604 to Mendel) are provided as a means of regulating circadian rhythm.

The present invention provides a method of regulating circadian rhythm by modulating the peripheral clock components in the vasculature by administering retinoid nuclear receptor ligands.

SUMMARY OF THE INVENTION

The present invention relates to the modulation of circadian rhythm through a retinoid nuclear receptor.

On object of the present invention provides a method of modulating a ligand-dependent interaction between retinoid nuclear receptors and the circadian clock transcription activators to directly affect core circadian clock function.

Another aspect of the present invention provides a method of screening for compounds that effect a phase-shift of the core circadian clock.

DETAILED DESCRIPTION OF THE INVENTION

Figure 1A:
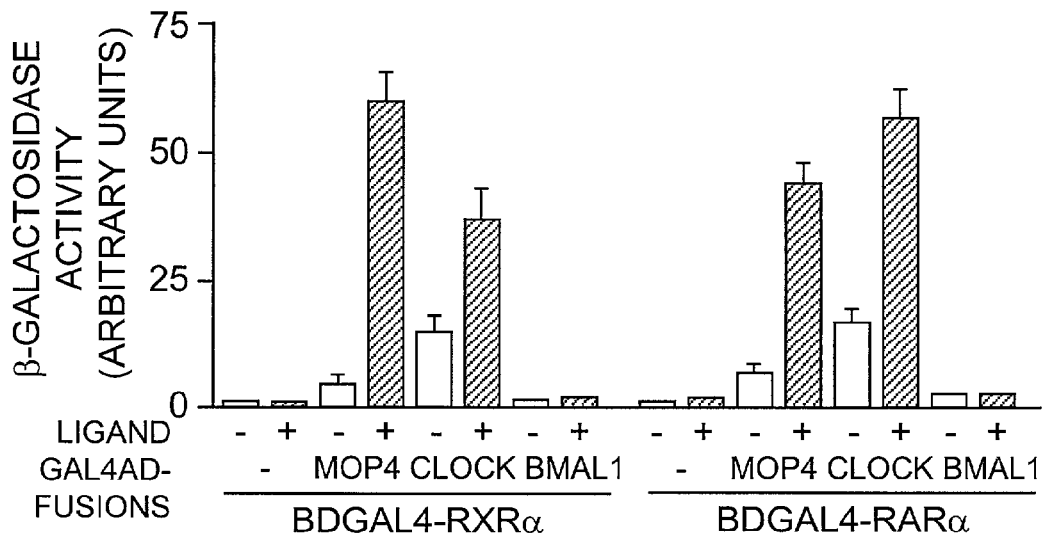
FIG. 1A demonstrates that retinoid nuclear receptor ligands increase the strength of the interaction between MOP4 and CLOCK with RXRα and RARα in YRG2 cells. All-trans retinoic acid (tRA, 1 μM), in the case of RARα, and 9-cis-retinoic acid (9cisRA, 1 μM), in the case of RXRα were added where indicated.

The mammalian circadian system is organized so that self-sustained oscillators in the SCN entrain peripheral oscillators by releasing a continuous stream of rhythmic signals (Yamazaki, et al. (2000) *Science* 288:682–685). It is to be understood by one skilled in the art that the phase and amplitude of peripheral clocks vary between different tissues and organs, in addition to differing from the phase and amplitude in the SCN. One function of the peripheral clock may be to generate a weak or dampened SCN signal, thus amplifying the oscillation of the signal in that peripheral tissue. In addition, peripheral clocks may locally coordinate gene expression. Every cell may have circadian clockwork, primed by the right environment, humoral or neural cue. A vascular clock may generate an amplified and synchronized vascular rhythm in response to uncoordinated blood-borne signals from central and peripheral clocks. These signals may be the diurnal release of catecholamines and steroids or the periodic bioavailability of signals such as vitamins associated with metabolic cycling.

The existence of multiple oscillators is a common characteristic of all circadian systems so far described in multicellular organisms. In a system where the constituent rhythms exhibit distinct phases, this may be the most effective way of generating the complex phase relationships among multiple overt rhythms that are known to exist and are almost certainly critical to normal function. Peripheral oscillators permit tuning of biological rhythms without difficulty to small, gradual changes in the phase of the input signal. If the change in phase, however, is completely disruptive, due to distorted environmental cures such as transatlantic air travel, the changeover from a day work schedule to a night work schedule, or a large hormonal release such as sympathoadrenal activation under conditions of severe stress, the phase relationships between SCN and peripheral clocks will be abolished, resulting in a temporarily and severely disorganized circadian system. Therefore, one aspect of the present invention provides a method of modulating the core clock oscillator by a modulating a peripheral clock. In a preferred embodiment, the peripheral clock is the vascular clock.

As light plays a key role in circadian clock rhythms, proteins binding to retinoid nuclear receptors, retinoid X receptor (RXRα) and retinoic acid receptor (RARα), were investigated. Using a yeast two-hybrid system, a yeast Gal4 activation domain (AD) fusion cDNA library from human aortic vascular smooth muscle cells (VSMC) was constructed to investigate novel nuclear receptor function in the vasculature. As bait in this assay, the ligand-binding domain of hRXRα was fused to the yeast Gal4-DNA binding domain (DBD). Analysis of 61 histidine and β-galactosidase positive clones revealed RXRα heterodimeric partners, such as peroxisome proliferator-activated receptor (PPARγ), RARα, and LXR, as well as coactivators, such as SRC-1 and RIP140 (Westin, et al. (2000) *Adv. Pharmacol.* 47:89–112). The bHLH-PAS protein, MOP4, was identified on five occasions as an RXRα-interacting clone. These five clones consisted of four separate cDNAs; two clones were identical. In addition to RXRα, MOP4 also interacted strongly with RARα, but not with other nuclear hormone receptor Gal4BD fusions such as PPARγ and LXR. Because MOP4 shares high homology with CLOCK and both proteins can heterodimerize with BMAL1, full-length cDNAs for CLOCK and BMAL1 were tested for possible interactions with RXRα and RARα. Both RXRα and RARα interacted strongly with CLOCK, but not its heterodimeric partner, BMAL1, suggesting the specificity of the interaction. Similarly, no interaction was observed between CLOCK or BMAL1 and PPARγ and LXR. In a preferred embodiment of the present invention, MOP4 or CLOCK interact with RXRα or RARα.

Figure 1B:
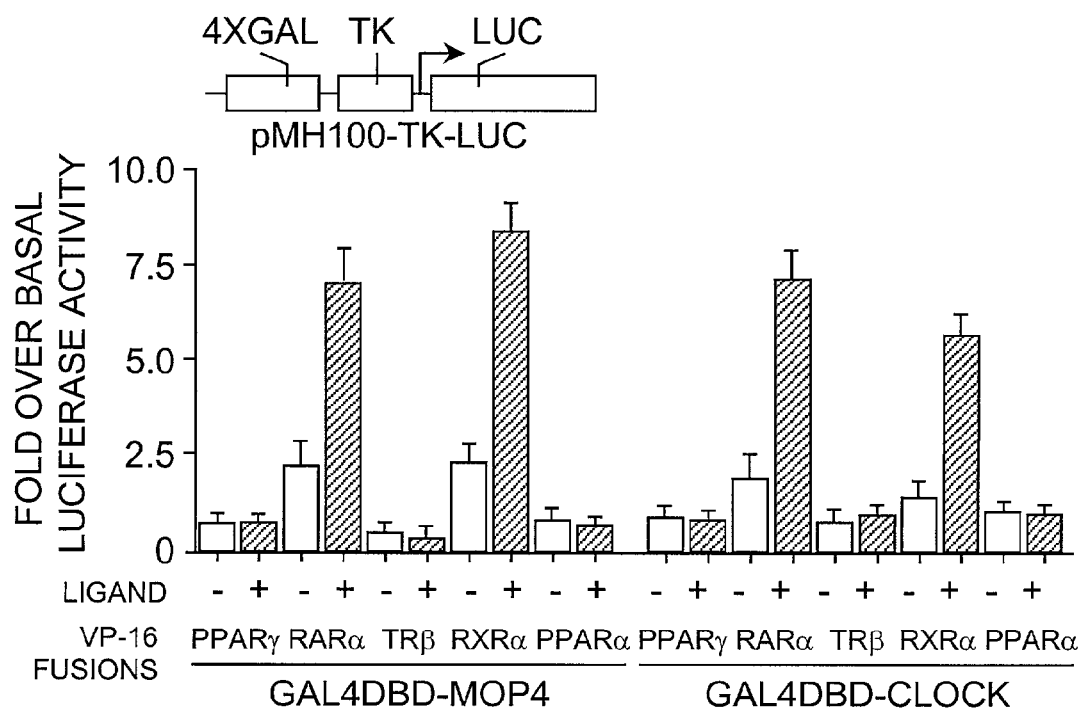
FIG. 1B demonstrates that MOP4 and CLOCK interact with RXRα and RARα in a ligand-dependent manner in mammalian cells. The ligands for PPARγ, RARα, TRβ, RXRα, and PPARα were 15dPGJ$_2$, tRA, T3 (1 μM), 9cisRA, and ETYA (10 μM), respectively.

A liquid β-galactosidase activity assay was utilized to assess the effect of ligands on these novel interactions. While RXRα and RARα alone interacted with CLOCK and MOP4, the strength of these interactions was increased up to 15-fold in the presence of ligand (FIG. 1A). To determine whether this interaction occurs in mammalian cells, a mammalian two-hybrid analysis was utilized and the results show a ligand-dependent interaction between Gal4DBD fusions of CLOCK and MOP4 with VP16 fusions RXRα and RARα. Consistent with yeast two-hybrid results, no interactions with PPARγ, TRβ, and PPARα were observed in the presence or absence of ligand (FIG. 1B). Together, these results suggest that RXRα and RARα can interact with MOP4 and CLOCK in intact yeast and mammalian cells and these interactions are stimulated by the presence of a ligand. Accordingly, another preferred embodiment of the present invention provides that MOP4 or CLOCK interact with RXRα or RARα in the presence of a ligand.

As one skilled in the art can appreciated, many subtypes of the two main retinoid nuclear receptors exist in mammals (and other organisms) and may bind to MOP4 and CLOCK. Within each type there are subtypes; in the RAR family the subtypes are: RARα RARβ, and RARγ; in the RXR family the subtypes are: RXRα, RXBβ, and RXRγ. Furthermore, proteins sharing homology with retinoid nuclear receptors are also to be considered relevant to the present invention. An example includes, but is not limited to, the retinoid-related orphan receptor (RORβ). It has also been established in the art that the distribution of the two main retinoid nuclear receptor types and several sub-types is not uniform in the various tissues and organs of mammalian organisms. Moreover, it is generally accepted in the art that many unwanted side effects of ligands are mediated by one or more of the RAR receptor subtypes. Accordingly, among ligands having agonist-like activity at retinoid nuclear receptors, specificity or selectivity for one of the main types or families, and even specificity or selectivity for one or more subtypes within a family of receptors, is considered a desirable pharmacological property. Some ligands bind to one or more RAR receptor subtypes, but do not trigger the response which is triggered by agonists of the same receptors. A ligand that binds to a biological receptor but does not trigger an agonist-like response is usually termed an antagonist. Accordingly, the "effect" of ligands on retinoid nuclear receptors may fall in the range of having no effect at all, (inactive ligand, neither agonist nor antagonist), the ligand may elicit an agonist-like response on all receptor subtypes (pan-agonist), or a ligand may be a partial agonist and/or partial antagonist of certain receptor subtypes if the ligand binds to but does not activate certain receptor subtype or subtypes but elicits an agonist-like response in other receptor subtype or subtypes. A pan antagonist is a ligand that binds to all known retinoid nuclear receptors but does not elicit an agonist-like response in any of the receptors.

Ligands useful in enhancing the interaction between MOP4 or CLOCK and retinoid nuclear receptors include, but are not limited to, all-trans retinoic acid (tRA), 9-cis-retinoic acid (9cisRA), vitamin A, docosahexaenoic acid (DHA), tetrahydronaphthalene derivatives as disclosed in U.S. Pat. No. 6,344,561 to Vuligonda, et al. (herein referenced in its entirety), and ligands disclosed in U.S. Pat. No. 6,320,074 to Boehm, et al. Ligands or derivatives thereof, can be natural or synthetic.

A GST-pulldown assay was performed to determine whether similar interactions can also be detected in vitro. Indeed, both MOP4 and CLOCK, but not BMAL1, were retained on GST-RXRα and GST-RARα-glutathione sepharose affinity matrices in vitro and nuclear receptor ligand further enhanced complex formation. Previously characterized retinoid nuclear receptor C-terminal truncated AF2 mutants, RXRΔ443 and RARΔ404 (Schulman, et al. (1996) *Mol. Cell Biol.* 16:3807–3813), were used to further investigate the ligand-dependent nature of this interaction. These mutants, which are defective in ligand-dependent function were unable to form complexes with CLOCK and MOP4. Ligand-dependent activity of these mutants was significantly reduced, consistent with the ability of ligand to enhance complex formation.

As BMAL1 heterodimerizes with both MOP4 and CLOCK, GST-RXRα pulldown assays were conducted with in vitro-labeled BMAL1 and MOP4 to evaluate the effect that BMAL1 has on the interaction of MOP4 with RXRα. While BMAL1 does not bind to RXRα, it did not diminish the ability of MOP4 to interact with RXRα. The addition of cold MOP4 to the BMAL1:GST-RXRα binding reaction facilitated retention of BMAL1, suggesting that MOP4, BMAL1 and RXRα may exist as a trimeric complex in vitro. Even at limiting amounts of MOP4, the presence of BMAL1 did not prevent its association with GST-RXRα. Thus, BMAL1 does not alter the affinity of MOP4 for RXRα or RARα. Similar results were also obtained for CLOCK. These results were extended by conducting coimmunoprecipitation experiments using coexpressed protein in vitro and in vivo. Incubation of anti-CLOCK or anti-RAR antibodies with in vitro translated CLOCK and RARα led to the coimmunoprecipitation of CLOCK and RARα. A ligand-dependent increase in association of both proteins was observed when incubations were carried out in the presence of retinoic acid. Furthermore, in vivo association between CLOCK and RARα was detected in cell lysates from NIH 3T3 cells transiently cotransfected with expression plasmids encoding full-length coding regions for hCLOCK and hRARα. Cell lysates were immunoprecipitated with anti-RAR antibody, and the immunoprecipitated material was blotted and probed with anti-CLOCK antibodies to assess interactions. Western blotting of the cell lysates prior to immunoprecipitation showed that both proteins were expressed at detectable levels. Together, these results demonstrate that CLOCK and MOP4, free or in its dimeric complex with BMAL1, can associate with nuclear receptors in vitro and in vivo and that this interaction is stimulated by ligand requiring the AF2 domain of nuclear receptors.

Figure 2A:
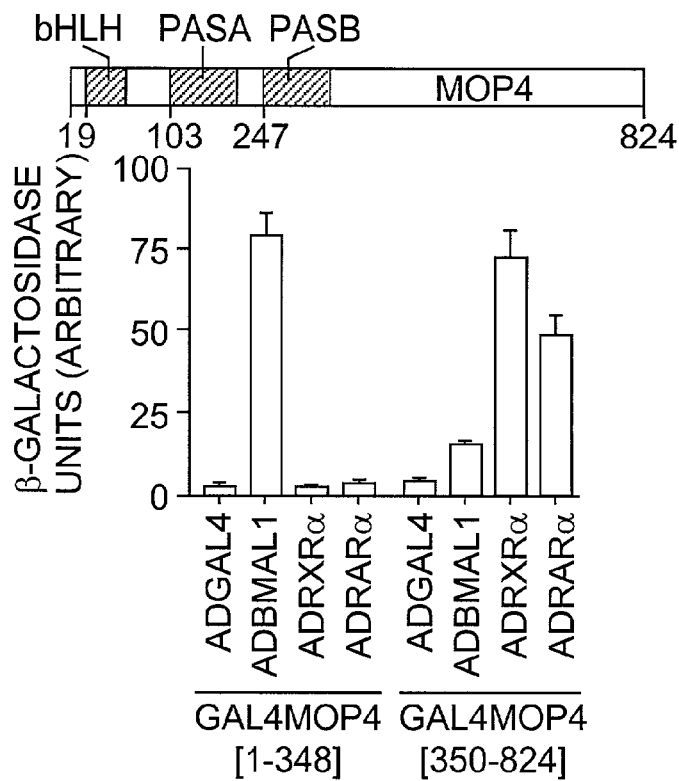
FIG. 2 demonstrates that the C-terminal regions of MOP4 and CLOCK are responsible for interacting with RXRα and RARα. Liquid β-galactosidase assays were performed in the presence or absence of ligand as indicated.
Figure 2B:
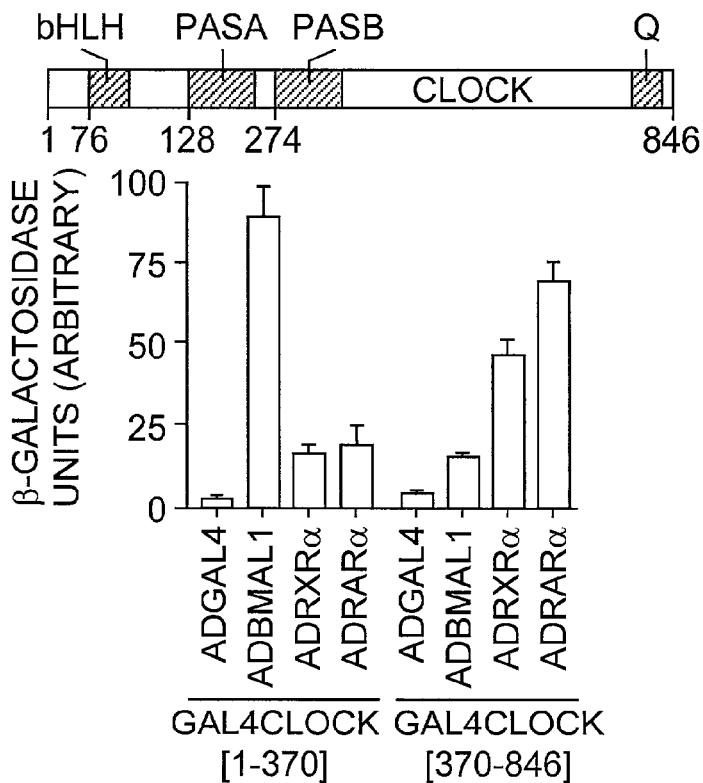

Mapping experiments were conducted to determine which domains of CLOCK and MOP4 interacted with the retinoid nuclear receptors. Both MOP4 and CLOCK harbor a short, basic helix-loop-helix domain immediately N-terminal to a 275 amino acid PAS domain which, in turn, contains two 50 amino acid repeats, termed PAS A and PAS B. These domains may function as dimerization surfaces (Huang, et al. (1993) *Nature* 364:259–262) and can serve as docking sites for cellular chaperones in other members of the bHLH-PAS family (Gu, et al. (2000) *Ann. Rev. Pharmacol. Toxicol.* 40:519–561). N- and C-terminal truncation mutants were generated for both CLOCK and MOP4 as Gal4BD fusions and used in mammalian two-hybrid assays to broadly map the nuclear receptor (NR) interaction domain. While the N-terminal bHLH-PAS domains showed on interaction, a very strong interaction between the C-terminal region (residues 350–824) of MOP4 and CLOCK (residues 370–846) with RXRα and RARα was observed (FIG. 2). However, the N-terminal mutant still retained the ability to interact with BMAL1 (FIG. 2, lanes 2 and 10). These results localize the NR interaction domains to the C-terminus of MOP4. For finer mapping, serial C-terminal deletion mutants were generated, in vitro labeled and analyzed for the ability to interact with nuclear receptors by GST-pulldown assays. MOP4Δ727, but not MOP4Δ624 was retained on sepharose beads coupled to a GST fusion of the ligand-binding domain of RXRα. Deletion of amino acids 665–680 severely reduced the ability of MOP4 to interact with RXRα. These assays localized the region of MOP4 necessary for interaction with NR to amino acids 665–680. Deletion mutants of CLOCK were also tested for their interaction with RXR. The region of CLOCK necessary for NR interaction was localized to amino acids 370–509. CLOCKΔ509 but not CLOCKΔ370 was retained on sepharose beads bound with GST-RXRα.

The region of MOP4 that bound to RXRα contained an LxxLL motif (amino acids 670–675). LxxLL is a common motif necessary for protein-protein interactions and are present in nuclear receptor cofactors (Westin, et al. (1998) *Nature* 395:199–202) and in the ligand-binding domains of some nuclear receptors (Glass, et al. (2000) *Genes Dev.* 14:121–141). The conserved leucines were mutated to alanines in the LxxLL motif of MOP4 (MOP4ΔAAA) to detect whether this motif was essential for the NR interactions. Mutating these three leucines to alanines blocked MOP4 from associating with GST-RXRα, suggesting a role of LxxLL motifs in modulating MOP4:RAR/RXR interactions. Accordingly, a preferred embodiment of the present invention provides that MOP4 or derivatives thereof contain one or more LxxLL motifs. p Although the NR interactions did not disrupt the interaction of either CLOCK or MOP4 with BMAL1, it was possible that it affected transcriptional activity of the heterodimers in vitro. MOP4 shares the highest homology of all members of the bHLH-PAS family with CLOCK. They are 50% homologous at the amino acid level, which increases to 75% homology in the bHLH-PAS domain. Both MOP4 and CLOCK transactivate genes via E-box elements as heterodimers with BMAL1. They have been shown to activate circadian responsive genes including AVP, Per1, and AA-NAT (Kume, et al. (1999) *Cell* 98:193–205; Chong, et al. (2000) *J. Biol. Chem.* 275: 32991–32998). Furthermore, cell culture experiments show that clock proteins mCRY1 and mCRY2 can inhibit the action of MOP4:BMAL1 heterodimers in vitro (Kume, et al. (1999) *Cell* 98:193–205). Studies with the *Drosophila* clock proteins indicate that the interaction of CLOCK and CYCLE, the *Drosophila* homolog of BMAL1, with negative regulator PER and TIM does not disrupt the CLOCK: CYCLE heterodimer, but prevents it from binding to an E-box (Lee, et al. (1999) *Mol. Cell Biol.* 19:5316–5325). Gel-shift analyses were performed to determine how the NR interaction might influence the ability of the heterodimer to bind to an E-box element. The MOP4:BMAL1 and CLOCK:BMAL1 E-box complexes were readily detected in the gel shift assay but the assembly of the bHLH-PAS heterodimer on the E-box consensus sequence was severely inhibited by increasing concentrations of ligand-bound RXRα and RARα. Moreover, this inhibition was shown to be ligand-dependent. These results are consistent with the in vitro results and demonstrate that interactions of RXRα or RARα with the MOP4:BMAL1 or the CLOCK:BMAL1 heterdimer reduces their ability to bind DNA.

Figure 3A:
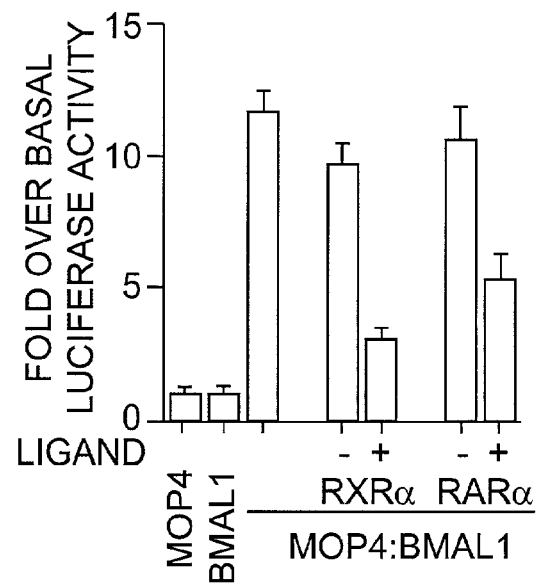
FIG. 3A demonstrates that overexpression of RXRα and RARα inhibits the MOP4:BMAL1-mediated E-box transactivation.
Figure 3B:
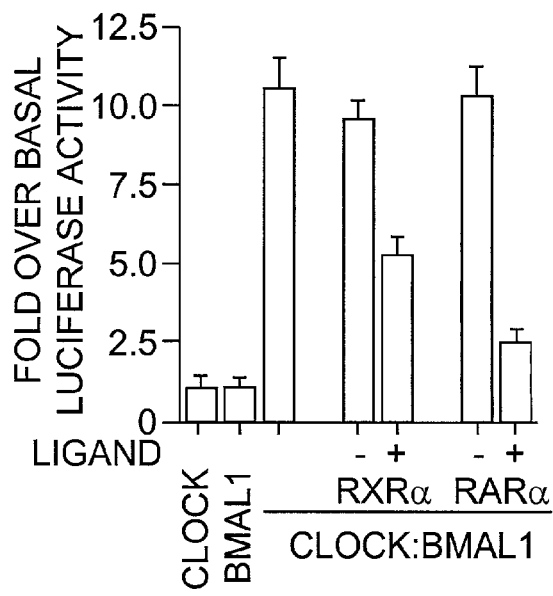
FIG. 3B demonstrates that overexpression of RXRα and RARα inhibits the CLOCK:BMAL1-mediated E-box transactivation.
Figure 3C:
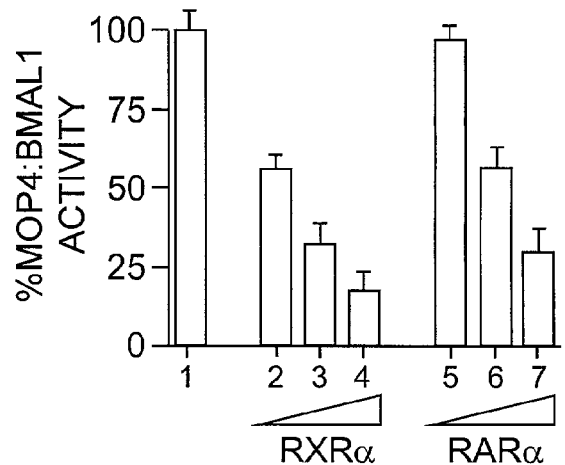
FIG. 3C demonstrates that RXRα and RARα inhibition of MOP4 E-box transactivation is dose-dependent. Experiments were conducted in the presence of ligand.
Figure 3D:
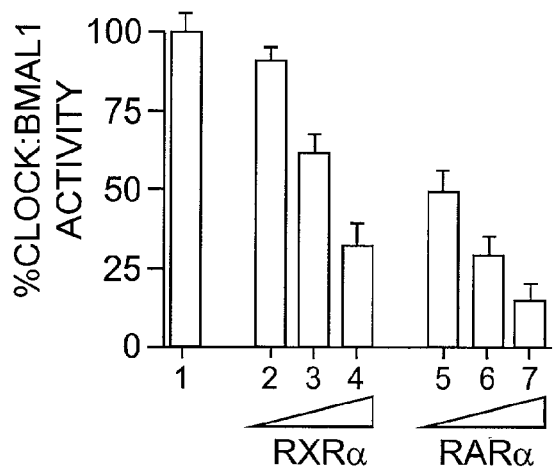
FIG. 3D demonstrates that RXRα and RARα inhibition of CLOCK E-box transactivation is dose-dependent. Experiments were conducted in the presence of ligand.

The effect of RXRα and RARα on E-box binding of MOP4 and CLOCK is consistent with a role for nuclear receptors in the negative limb of the circadian feedback loop. This was examined by directly analyzing the effect of overexpression of the retinoid nuclear receptors on E-box-induced gene transcription in vivo. A luciferase reporter construct containing three E-boxes (CACGTG) was used for this purpose (Hogenesch, et al. (1998) *Proc. Natl. Acad. Sci. USA* 95:5474–5479). As previously reported, both MOP4: BMAL1 and CLOCK:BMAL1 activate transcription via an E-box-dependent mechanism (Kume, et al. (1999) *Cell* 98:193–205). Importantly, overexpression of RXRα and RARα inhibited MOP4 and CLOCK-mediated luciferase reporter gene activation in a ligand-dependent fashion (see FIG. 3A and FIG. 3B, compare lanes 4 with 5 and 6 with 7). This effect was also dose-dependant (see FIG. 3C and FIG. 3D). RXRα had a stronger inhibitory effect towards the MOP4:BMAL1 heterodimer, reducing its E-box activation by roughly 80% at the highest concentration used. On the other hand RARα was the more potent inhibitor of CLOCK: BMAL1, maximally inhibiting activation to a similar extent (FIG. 3C and FIG. 3D). The reason for this preference is currently unknown. In a preferred embodiment of the present invention, ligand-bound nuclear receptor inhibits transcriptional activator binding to E-boxes and thus transcriptional activity from the E-box containing promoter.

Figure 3E:
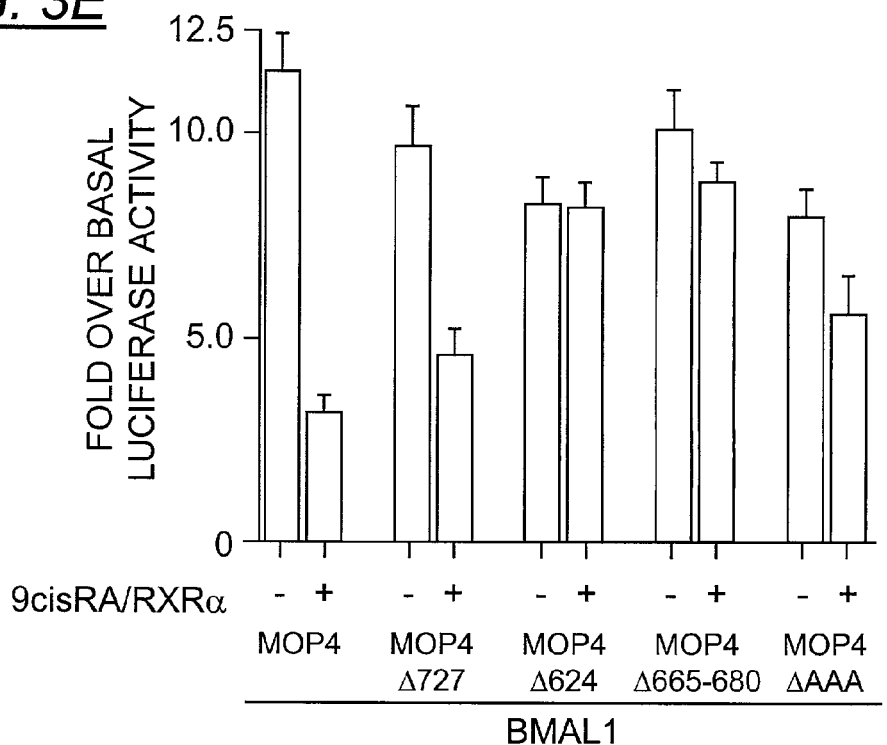
FIG. 3E demonstrates that MOP4 mutants are not sensitive to inhibition by ligand-bound RXRα.

Human CRY2 functions as a negative regulator of the circadian feedback loop (Kume, et al. (1999) *Cell* 98:193–205). Consistent with previous observations, hCRY2 caused 90% inhibition of both CLOCK:BMAL1 and MOP4:BMAL1-induced transcription. Finally, the effects of RXRα on the ability of mutant forms of MOP4, MOP4Δ727, MOP4Δ624, MOP4Δ665–680 and MOP4ΔAAA to activate reporter gene expression was analyzed. As expected, MOP4Δ727 and MOP4Δ665–680 retained the ability to fully activate the reporter in the presence of BMAL1 (FIG. 3E, Lanes 3 and 7), while MOP4Δ624 and MOP4ΔAAA were roughly 30% less effective (FIG. 3E, lanes 5 and 9). MOP4Δ727 remained susceptible to inhibition by RXRα, which is consistent with this mutant having an intact NR interaction domain. However, MOP4Δ624 and MOP4Δ665–680 were no longer sensitive (FIG. 3E, lanes 6 and 8) and MOP4ΔAAA was >50% less sensitive to nuclear receptor-mediated inhibition (FIG. 3E, lane 10). Such diminution of the inhibitory effects of RXRα, in the absence of the NR domain in MOP4, are consistent with the GST-pulldown assay results and suggest that the carboxy-terminus of MOP4 is necessary for its interaction and nuclear receptor-mediated inhibition.

Figure 4:
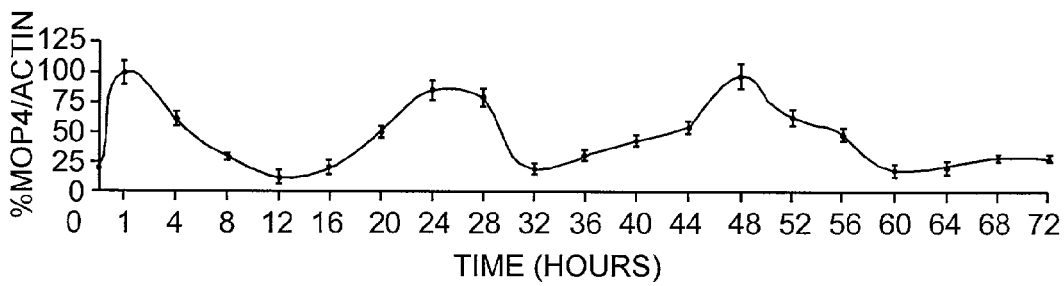
FIG. 4 shows that in a ribonuclease protection analysis of VSMC mRNA following serum shock, MOP4 transcript oscillates.

Expression of MOP4 is reportedly very low in the SCN (Shearman, et al. (1999) *Neuroscience* 89:387–397) and there are no reports of its cyclical expression, making it difficult to place MOP4 in the core oscillatory loop. The present invention demonstrates that MOP4 is strongly expressed in human vascular smooth muscle cells (VSMC) and that it cycles after serum shock. Northern blot analysis was performed on CLOCK, BMAL, CRY2, and MOP4. Strong signals were detected for CLOCK, BMAL, and CRY2 in human brain, heart, VSMC, spinal chord, and skeletal muscle tissues. MOP4 was present in the brain tissue and in spinal chord as previously demonstrated (Zhou, et al. (1997) *Proc. Natl. Acad. Sci. USA* 94:713–718), but the highest level of expression was evident in VSMC and in placenta, which is a highly vascular tissue. BMAL expression cycles in rat central and peripheral organs (Oishi, et al. (1998) *Biochem. Biophys. Res. Commun.* 253:199–203), while clock mRNA reportedly does not display a robust rhythm in the SCN of mice (Shearman, et al. (1999) *Neuroscience* 89:387–397). Ribonuclease protection analysis was performed after serum shock (Balsalobre, et al. (1998) *Cell* 93:929–937) to determine whether MOP4 expression fluctuates rhythmically in vascular smooth muscle cells. MOP4 mRNA expression cycled in a circadian pattern with peaks at 24 and 48 hours in VSMC (FIG. 4), consistent with it having a role in the vascular clock.

Figure 5A:
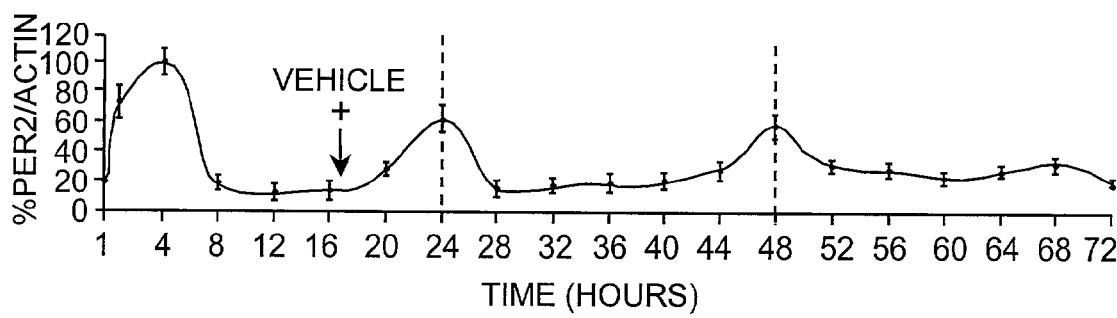
FIG. 5A shows that in a ribonuclease protection analysis of VSMC mRNA following serum shock and addition of vehicle at T17, hPER2 transcript oscillates.
Figure 5B:
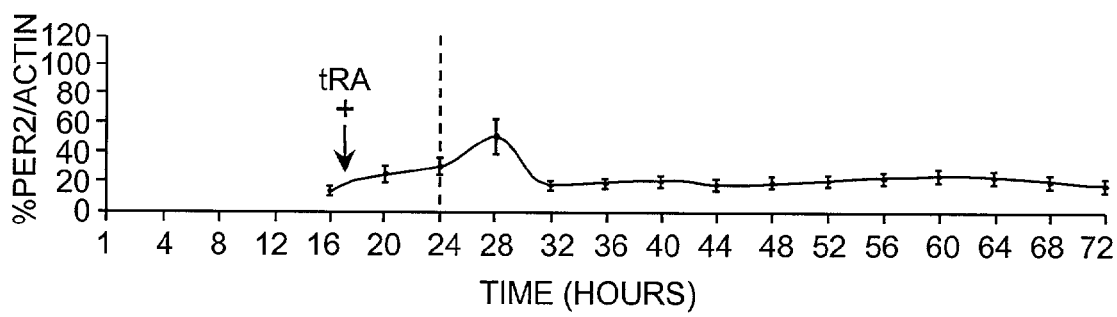
FIG. 5B shows hPER2 transcript oscillation is delayed after addition of tRA at T17.
Figure 5C:
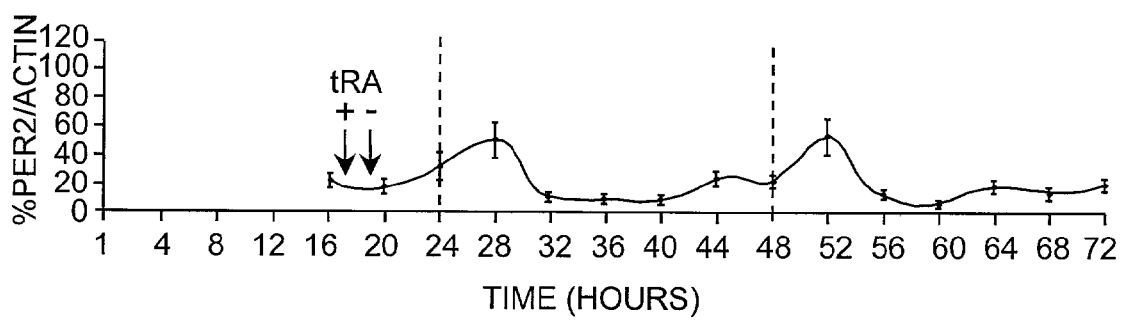
FIG. 5C shows hPER2 transcript oscillation is altered after addition of tRA at T17 and subsequent removal at T19.

The physiological relevance of nuclear receptor-mediated inhibition of CLOCK and MOP4 transcriptional gene activation comes from the demonstration that serum-induced cycling of hPer2 can be abolished or phase-shifted by a nuclear receptor ligand, depending on the duration and time of hormone treatment. In these experiments, it was determined that oscillating clock gene expression could be induced by serum shock in VSMC as had been reported in Rat and 3T3 fibroblasts (Balsalobre, et al. (1998) *Cell* 93:929–937; Akashi, et al. (2000) *Genes Dev.* 14:645–649). Following addition of 50% serum for two hours, hPER2 mRNA peaks very rapidly at T4 (fours hours after serum shock) and enters a cyclical expression pattern, peaking at T24 and T48 (FIG. 5A). Adding tRA at T17 and leaving it in the culture for the remainder of the experiment, delayed the peak of hPER2 mRNA from T24 to T28. Subsequently, hPER2 levels dropped and did not peak again for the remainder of the experiment (FIG. 5B). When tRA was added at T17 and removed at T19, the first hPER2 peak was again delayed to T28. However, the drop in hPER2 levels was followed by an increase, resulting in a second cycle which peaked at T52 (FIG. 5C). Thus, tRA phase delayed the hPER oscillation by four hours, which is consistent with the observation that ligand-bound RARα prevents CLOCK:BMAL1 heterodimer from activating transcription through its E-box. Removal of the ligand restored the ability of the CLOCK:BMAL1 heterodimer to induce hPER2 expression, but the phase of the cycle was delayed.

Figure 5D:
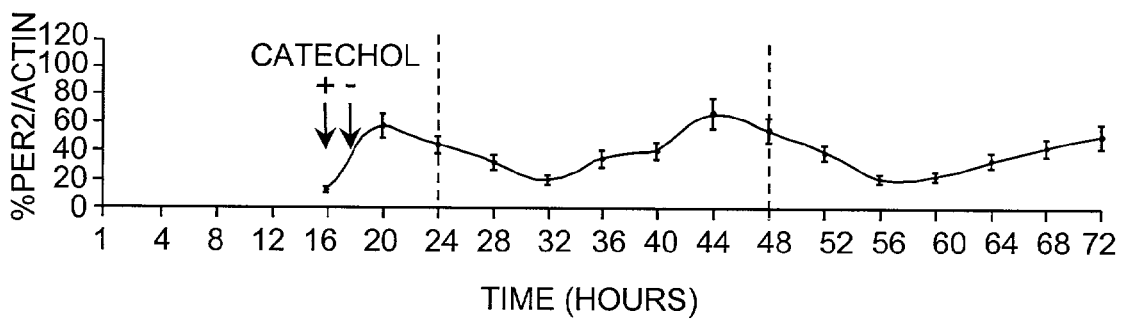
FIG. 5D shows hPER2 transcript oscillation is altered after addition of catecholamines at T16 and subsequent removal at T18.

The coincidental circadian variability of catecholamines and blood pressure (Hossmann, et al. (1980) *Cardiovasc. Res.* 14:125–129) led to the investigation of whether catecholamines can phase-shift a core clock oscillator in VSMC. Norepinephrine and epinephrine (10 μM), were added at T16 and left in the culture until T18. This phase advanced the hPER2 mRNA peak to T20 instead of T24 (FIG. 5D). These results provide an additional example of phase-shifting by circulating hormones and suggest that retinoids may phase-shift the vascular clock through regulation of the negative limb of the circadian feedback loop.

Based on these results, RXRα and RARα play a role in the negative limb of the circadian feedback loop by interacting with CLOCK and MOP4 and preventing their ability to drive E-box-mediated Per transcription. It remains to be determined whether this effect is restricted to the periphery or is also operable in the brain. Involvement of MOP4 in this peripheral oscillator, but not in the SCN clock, illustrates that some components of the feedback loop exhibit tissue-specific expression, perhaps facilitating site-specific responses to humoral stimuli. Dexamethasone has recently been reported to phase-shift the mPer rhythm in organs (Balsalobre et al. (2000) *Science* 289:2344–2347). The observations presented in the present invention are consistent with this finding and afford a molecular mechanism whereby such a nuclear hormone could change the phase of a core clock oscillator.

Another aspect of the present invention provides a method of screening for ligands that cause a phase-shift of a circadian rhythm. The invention provides methods for screening bioactive agents (the term "agent" and grammatical equivalents thereof being used interchangeably with the term "ligand" and the grammatical equivalents thereof) that are capable of binding to a retinoid nuclear receptors wherein a retinoid nuclear receptor and a candidate bioactive agent are combined. The binding of the candidate bioactive agent is then determined. Binding assays using a desired binding protein, immobilized or not, are well known in the art and may be used for this purpose using a retinoid nuclear receptor of the invention. Purified cell-based or protein-based (cell free) screening assays may be used to identify such bioactive agents. For example, a retinoid nuclear receptor protein may be immobilized in purified form on a carrier and binding to purified retinoid nuclear receptor protein may be measured in the presence and in the absence of potential bioactive agents. A suitable binding assay may alternatively employ a soluble form of a retinoid nuclear receptor of the invention.

In such a screening assay, a first binding mixture is formed by combining 9cisRA or a derivative thereof and RXRα protein, and the amount of binding in the first binding mixture ($B_0$) is measured. A second binding mixture is also formed by combining 9cisRA or a derivative thereof, RXRα, and the bioactive agent to be screened, and the amount of binding in the second binding mixture (B) is measured. The amounts of binding in the first and second binding mixtures are compared, for example, by performing a calculation of the ratio $B/B_0$. A compound or agent is considered to be capable of inhibiting binding if a decrease in binding in the second binding mixture as compared to the first binding mixture is observed. The formulation and optimization of binding mixtures is within the level of skill in the art, such binding mixtures may also contain buffers and salts necessary to enhance or to optimize binding, and additional control assays may be included in the screening assay of the invention. Compounds found to reduce the binding activity of human 9cisRA to RXRα or its fragment to any degree, preferably by at least about 10%, more preferably greater than about 50% or more, may thus be identified and then secondarily screened in other binding assays and in vivo assays. By these means agents capable of interfering with the binding of retinoid nuclear receptors, or of modulating the activity of a retinoid nuclear receptor, may be identified. Such screening methods are capable of identifying ligands that have pharmacological (pharmaceutical) activity. Pharmaceutical formulations comprising such pharmacologically active ligands and methods of administering the same are another aspect of this invention. Yet another aspect of the present invention is the use of a pharmacologically active compound identified by the methods described herein for the manufacture of a medicament for the prophylactic or therapeutic use in a subject.

EXAMPLES

Example 1

Plasmid and Proteins

For yeast, bacterial, and eukaryotic expression constructs, fragments of hMOP4, hCLOCK, hBMAL1, hPER2, HCRY2, hRXRα, hRARα, hPPARγ, hPPARα, hTRβ, and hβ-Actin were PCR-amplified using standard protocols and primers and cloned into pBDGAl4, pADGal4 (Stratagene, La Jolla, Calif.), pGEX4T (Amersham Pharmacia Molecular Dynamics, Piscataway, N.J.), CMX-PL1, CMXGal4, pCNDA3.1, and pCRII (Invitrogen™, Carlsbad, Calif.) using standard methods. Full-length cDNAs for MOP4, MOP3, and CLOCK were kindly provided by Dr. J. Hogenesch, hNPAS2 was a gift from Dr. D. Russell, and hCRY2 was generously provided by Dr. A. Cashmore. pGL3M34-LUC was a gift from Dr. C. A. Bradfield (Hogenesch, et al. (1998) Proc. Natl. Acad. Sci. USA 95:5474–5479) and pMH100-TK-Luc was a gift from Drs. R. Evans and B. Forman (Forman, et al. (1995) Cell 81:541–550). Sequences of all constructs flanking the cloning sites were verified by automated sequencing. Recombinant proteins were expressed in BL(21) (DE53) E. coli cells (Stratagene, La Jolla, Calif., purified using glutathione beads (Amersham Pharmacia Molecular Dynamics, Piscataway, N.J.). MOP4ΔAAA was constructed by converting the three leucines AA640–644 to alanines using a modified version of Quick Change Site-Directed Mutagenesis Kit (Stratagene, La Jolla, Calif.) exactly as described by Wang, et al. (1999) Biotechniques 26:680–682).

Example 2

Yeast Two-Hybrid Analysis

The yeast strain YRG2 (Stratagene, La Jolla, Calif.), transformed with the yeast expression plasmid pBDGAl4cam (Stratagene, La Jolla, Calif.) fused to hRXα (nt 670–1463 of accession number NM_002957), was used to screen a yeast Gal4 activation domain (AD) fusion cDNA library from human aortic vascular smooth muscle cells. The library was prepared by ligating XhoI/EcoRI-adapted, phosphorylated, oligo-dT-primed cDNA, prepared from polyadenylated RNA extracted from $1\times10^8$ human aortic vascular smooth muscle cells (Cambrex Corporation, East Rutherford, N.J.), into the HybriZAP® II vector and packaged with Gigapack® III Gold packaging extract (Stratagene, La Jolla, Calif.) into a primary lambda library. The primary library had $2.3\times10^6$ independent clones and had an average insert size of 2.5 kb. The primary library was amplified and mass excised and cloned into the pADGal4 phagemid vector, which was transformed in YRG2 containing pBDGal4RXRα, using a standard lithium acetate transformation procedure (Gietz, et al. (1992) Nucl. Acids. Res. 20:1425). RXRα-interacting clones were selected on media lacking tryptophan, leucine, and histidine, supplemented with 10 mM 3-amino-triazol. Surviving colonies were assayed for β-galactosidase activity using a colony filter lift assay in the presence of 5-bromo-4-chloro-3-indolyl β-D-galactoside (X-GAL) as described by Breeden, et al. ((1985 Cold Spring Harb. Symp. Quant. Biol. 50:643–650). The cDNAs from β-galactosidase-positive clones were sequenced across the Gal4/library cDNA boundary and analyzed using the BLAST algorithm at the NCBI. Liquid β-galactosidase assays were carried out exactly as described by Estojak, et al. ((1995) Mol. Cell. Biol. 15:5820–5829).

Example 3

In vitro Interactions Assays

In vitro, [$^{35}$S]methionine-labeled MOP4, CLOCK, BMAL1, and all of the MOP4 and CLOCK truncated and deletion mutants were synthesized using the CMX plasmids in a coupled transcription-translation system (TNT®, Promega Corporation, Madison, Wis.). Cold protein was prepared by using 1 mM methionine and omitting the [$^{35}$S]methionine-label. For GST-pulldown assays, in vitro-labeled proteins were incubated with glutathione separose bound GST, GST-RXRα, GST-RARα, GST-RXRΔ443, or GST-RARΔ404, for 2 hours at 4° C. in buffer containing 20 mM HEPES, pH 7.6, 200 mM NaCl, 1 mM EDTA, 4 mM MgCl$_2$, 1 mM DTT, 0.2% NP-40, 10% Glycerol, 10 µg/mL BSA and Complete protease inhibitor cocktail (Roche Molecular Biochemicals, Indianapolis, Ind.). Beads were washed extensively and bound proteins separated by SDS-polyacrylamide gel electrophoresis (SDS-PAGE) and analyzed by a PhosphorImager.

Example 4

In vitro Immunoprecipitations

[$^{35}$S]Methionine-labeled RARα and CLOCK were incubated with purified CLOCK and RARα protein, respectively for 30 min. at room temperature in the presence or absence of tRA. The complex was immunoprecipitated using anti-CLOCK and anti-RAR antibodies (Santa Cruz Biotechnology, Inc., Santa Cruz, Calif.) and protein A-agarose (Gibco, Carlsbad, Calif.) was added. Beads were washed extensively and bound proteins separated by SDS-PAGE and analyzed by a PhosphorImager.

Example 4

In vitro Immunoprecipitations

NIH 3T3 cells ($1.2\times10^6$) were seeded in 100 mm dishes and cotransfected with CLOCK and RAR mammalian expression vectors. After 14 hour, cells were treated with 1 µM tRA and 48 post-transfection cells were harvested and lysed in immunoprecipitation buffer (20 mM HEPES, pH 7.5, 100 mM KCl, 2.5 mM EDTA, 5 mM DTT, 2.5 mM PMSF, 0.05% Triton X-100, 10% glycerol, and Complete protease inhibitor cocktail (Roche Molecular Biochemicals, Indianapolis, Ind.). After centrifugation, supernatant was incubated with cross-linker, DTSSP (final concentration 3 mM) (Pierce Chemical Company, Rockford, Ill.) at room temperature for 30 min. Anti-RAR antibodies were added and the incubation continued for 3 hour at 4° C. Protein A-agarose beads were added and an additional 1 hour incubation at 4° C. followed. The immunoprecipitate was washed extensively and boiled for 5 min at 100° C. and bound proteins separated by SDS-PAGE, tranferred to membrane, and incubated with anti-CLOCK antibodies. The blots were probed with alkaline phosphatase-conjugated donkey anti-goat antibodies (Santa Cruz Biotechnology, Inc., Santa Cruz, Calif.).

Example 5

EMSA Assay

A double-stranded [$\gamma^{32}$P]dATP-labeled consensus oligonucleotide, GGGACACGTGACCC (SEQ ID NO:1) (CyberSyn Inc., Lenni, Pa.) was incubated for 30 min at 4° C. in a buffer containing 150 mM KCl, 20 mM Tris-HCl, pH 7.6, 5 mM MgCl$_2$, and 200 ng poly(dI-dC) in the presence of reticulocyte lysate expressed MOP4, CLOCK, BMAL1, and RXRα or RARα in the presence of 1 µM tRA or 1 µM 9cisRA (Sigma Chemicals, St. Louis, Mo.) where indicated. The samples were loaded directly onto 4% polyacrylamide-TBE gels to separate MOP4/CLOCK:BMAL1 bound DNA from free DNA. The gels were dried and analyzed on a PhosphorImager.

Example 6

Transfection Studies and Mammalian Two-Hybrid Analysis

NIH 3T3 cells were seeded at 20,000 cells/well in a 48-well dish and transfected by FuGENE™ liposome-mediated transfer (Roche Molecular Biochemicals, Indianapolis, Ind.) with internal control pRLSV40 (5 ng), pGL3M34 reporter, CMX-MOP4 (100 ng) or CMX-CLOCK (100 ng) and CMX-BMAL1 (100 ng) in the presence or absence of CMX-RXRα or CMX-RARα (25–100 ng). CMX-MOP4ΔAAA (100 ng), pCDNA3.1MOP4Δ727 (100 ng), pCDNA3.1MOP4Δ624 (100 ng), and CMX-MOP4Δ635–645 (100 ng) were used instead of CMXMOP4 where indicated. The amount of DNA in each transfection was kept constant by addition of empty pCDNA3 vector. The media were replaced approximately 14 hour after transfection with fresh Dulbecco's modified Eagle's medium and tRA (1 µM) or 9cisRA (1 µM) (Sigma Chemicals, St. Louis, Mo.) where indicated. Forty-eight hours post-transfection, cells were harvested to determine luciferase activity by luminometry (Dual-Luciferase® Reporter Assay System, Promega Corporation, Madison, Wis.). The procedure for mammalian two-hybrid analysis was identical except that CV-1 cells were used. MH100TK-LUC (100 ng) reporter, CMX-Gal4DBD-MOP4 (20 ng), CMX-Gal4DBD-CLOCK (20 ng) in the presence of, CMX-VP16-PPARγ (20 ng), CMX-VP16-RARα (20 ng), CMX-VP16-TRβ (20 ng), CMX-RXRα (20 ng) or CMX-VP16-PPARα (20 ng). The ligands tRA, 9cisRA, 3,5,3'-triiodo-L-thyronine (T3), 15-deoxy-Δ1214 prostaglandin J2 (15dPGJ2) (all 1 µM), 5,8,11,14-Eicosatetraynoic Acid (ETYA; 10 µM) (Sigma Chemicals, St. Louis, Mo. and Cayman Chemical Company, Ann Arbor, Mich.) were added where indicated. For all the figures, each value is the mean of three independent experiments +/− standard error. Each experiment included six replicates from a single assay.

Example 7

Northern Analysis

Polyadenylated (Poly [A$^+$]) RNA was extracted from VSMC using FastTrack® 2.0 kit (Invitrogen™, Carlsbad, Calif.). Brain, Spinal Chord, Heart and Skeletal Muscle Poly [A$^+$] RNA was purchased from Clontech (Palo Alto, Calif.). Poly [A$^+$] was separated by electrophoresis in a 1% agarose-formaldehyde gel, blotted onto Hybond™ N$^+$ (Amersham Pharmacia Molecular Dynamics Biotechnology, Piscataway, N.J.), and hybridized with random prime-labeled probe (S.A.=2×10$^6$ cpm/mL). The blots were hybridized with ULTRAhyb™ hybridization solution (Ambion, Austin, Tex.) and washed following the manufacturer's protocol. Probes used were hMOP4 (accession number U51625), hBMAL1 (accession number U51627), hCLOCK (accession number NM_004898), and hCRY (accession number AB014558). The probe for hGAPDH was purchased from Clontech (Palo Alto, Calif.). Blots were exposed at −80° C. to BioMax film (Kodak, Rochester, N.Y.) with two intensifying screens.

Example 8

Serum Shock and RPA Analysis

VSMC (3500 cells/cm$^2$) were plated on 10 cm$^2$ plates 6 days before the experiment and were serum-starved for 48 hours after reaching confluence. Serum shock was carried out using 50% fetal bovine serum (Gibco, Carlsbad, Calif.) as previously described (Balsalobre, et al. (1998) Cell 93:929–937) and cells were harvested at the indicated time points and stored at −80° C. Total RNA was extracted from each sample using the RNAwiz™ reagent (Ambion, Austin, Tex.). Probes were prepared for hMOP4 (nt 2459–2760 of accession number U51625), hactin (nt 547–810 of accession number NM_001101) and hPER2 (nt 428–794 of accession number AB012612) by RT-PCR (Reverse Transcriptase System, Promega Corporation, Madison, Wis.; Expand High Fidelity Taq DNA Polymerase, Roche Molecular Biochemicals, Indianapolis, Ind.) from Placenta total RNA (Ambion, Austin, Tex.). The PCR products were cloned into pCRII (Dual Promoter TOPO® TA cloning kit, Invitrogen™, Carlsbad, Calif.). Antisense RNA probes were prepared by in vitro transcription of the linearized templates with T7 or SP6 RNA polymerase using 32P-labeled UTP (MAXIscript™, In Vitro Transcription Kit, Ambion, Austin, Tex.). RNA (5 µg) from each time point was hybridized for 16 hour with 8×10$^4$ cpm of the probe at 42° C. and digested with RNaseA/T1 (SequaGel System, National Diagnostics, Atlanta, Ga.), dried and analyzed by a PhosphorImager. The data was quantitated using ImageQuant version 1.2 software (Amersham Pharmacia Molecular Dynamics, Piscataway, N.J.) All results represent a mean of at least two independent experiments and are expressed as the ratio of the MOP4 or PER2 signal divided by the Actin signal at the same time point.

What is claimed is:

1. A method for inducing a circadian rhythm phase-shifting effect in a mammal in need thereof comprising identifying a mammal in need of circadian rhythm phase-shifting and administering to the mammal an agonist which binds a retinoid X receptor or retinoic acid receptor thereby inducing a circadian rhythm phase-shift in the mammal.

2. The method of claim 1 wherein the agonist comprises all-trans retinoic acid or 9-cis-retinoic acid.

3. The method of claim 1 wherein the retinoid nuclear receptor interacts with a transcriptional activator of the core circadian clock thereby inhibiting DNA binding activity.

4. The method of claim 3 wherein a transcriptional activator of the core circadian clock comprises CLOCK or MOP4.

5. A method of modulating a peripheral clock in a mammal in need thereof comprising modulating a retinoid nuclear receptor.

6. The method of claim 5 wherein the peripheral clock is a vascular clock.

* * * * *

SEQUENCE LISTING

<160> NUMBER OF SEQ ID NOS: 1

<210> SEQ ID NO 1
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 1
gggacacgtg accc     14